(12) United States Patent
Long

(10) Patent No.: US 6,652,846 B2
(45) Date of Patent: Nov. 25, 2003

(54) ATTRACTANTS FOR YELLOW JACKETS

(76) Inventor: Roger H. Long, 673 Gilchrist Ct., Hernando, FL (US) 34442

(*) Notice: Subject to any disclaimer, the term of this patent is extended or adjusted under 35 U.S.C. 154(b) by 0 days.

(21) Appl. No.: 09/730,878

(22) Filed: Dec. 7, 2000

(65) Prior Publication Data

US 2002/0114822 A1 Aug. 22, 2002

Related U.S. Application Data

(60) Provisional application No. 60/199,808, filed on Apr. 26, 2000.

(51) Int. Cl.[7] .................. A01N 37/02; A01N 63/00; A01N 43/04

(52) U.S. Cl. .................. 424/84; 424/520; 424/553; 424/581; 514/557; 514/21; 514/23; 514/53; 514/54; 426/1

(58) Field of Search .................. 424/84, 520, 553, 424/581; 514/557, 21, 23, 53, 54; 426/1

(56) References Cited

U.S. PATENT DOCUMENTS 6,083,498 A * 7/2000 Landolt .................. 424/84

* cited by examiner

Primary Examiner—John Pak

(57) ABSTRACT

The invention relates to attractants for use in yellow jacket traps. The attractants have improved overall effectiveness in attracting yellow jackets, in attracting a broader spectrum of yellow jacket species and in attracting yellow jackets in the several phases of their life cycles when their food requirements vary. The attractants are distinguished by the inclusion of a weak acid in the attractant formulation. The preferred weak acid is acetic acid and its preferred form is a vinegar.

15 Claims, No Drawings

US 6,652,846 B2

ATTRACTANTS FOR YELLOW JACKETS

HISTORY OF THE APPLICATION

This application is based upon and claims priority from U.S. Provisional Patent Application Ser. No. 60/199,808 filed Apr. 26, 2000.

TECHNICAL FIELD

The invention relates to attractants for yellow jackets and their use in traps for yellow jackets. The attractants have improved overall effectiveness in attracting yellow jackets, in attracting a broader spectrum of yellow jacket species and in attracting yellow jackets in the several phases of their life cycles when their food requirements vary.

Yellow jackets are of the genus Vespa of which there are about 30 species in North America. Of these, the more common of the North American yellow jackets are *Vespula vulgaris, Vespula rufa, Vespula germanica* (mostly found in northeastern states); *Vespula pensylvanica* (mostly found in western states) and *Vespula squamosa* (mostly found in southern states.) These species are aggressive and may attack people without particular provocation. Note in passing that in Europe yellow jackets are usually referred to as "European wasps."

BACKGROUND ART

The life cycle of the yellow jacket begins in the early spring when an over-wintering mated queen is nested. The queen feeds on carbohydrates such as nectar and gathers high protein substances as larval food for the first brood of workers. After emergence of the workers, however, she remains in the nest. During late spring and summer, as subsequent broods of larvae are reared and established, increasing quantities of high protein materials are needed to support the yellow jacket colonies. In the summer new queens and males are produced in the colony and emerge to find mates as when exploring flowers for nectar. The new queens mate and almost immediately find a site in which to hibernate over the winter until the following year.

Yellow jackets are aggressive when searching for food and, on occasion, can make a small area almost uninhabitable for humans. This condition can exist, for example, at camp and picnic sites, restaurants, zoos or other locations where yellow jackets congregate to scavenge exposed food or garbage.

One method used to reduce the population of yellow jackets is to entice workers of the scavenging species to enter baited traps. The traps contain attractants (bait) which lure the yellow jackets into the traps. The literature sometimes refers to chemical attractants to distinguish them from food and nutritional attractants. Since the distinction between the two is not always clear, and since the distinction serves little purpose in understanding or practicing the herein described invention, the terms "attractant(s)" and "bait" are used generically in the specification and the attached claims to include materials that arouse the interest of yellow jackets and lure them into traps. Traps making use of chemical attractants have the advantage of needing less attention than do those with food attractants since chemicals are less likely to spoil and rot than are conventional meat and fish attractants.

Traps are basically of two different types and functionality. One type of trap allows yellow jackets to enter easily enter but confuses them in finding their way out. Most of these types of traps make use of a screen rolled into a cone open at both its top and bottom, much like a megaphone. The workers may readily find their way into the traps through the large end of the cone but difficulty, in finding their way back out through the narrower opening. The same effect can be obtained by locating a series of small openings, often on the lid of the trap, that are just large enough to let yellow jackets enter the trap, but too small to let them find their way back out. Eventually the trapped yellow jackets die from lack of food and water. For convenience these traps are referred to as "dry" traps.

A second kind of trap may be referred to a "wet" trap. A wet trap has a liquid at the bottom of the trap to which an insecticide has been added or is a drowning fluid. The insecticides kill the yellow jackets in the trap. The drowning fluid—water to which a surfactant has been added—"wet out" the wings and body of the insect so that it cannot fly and the insect drowns in the water. The attractants of the instant invention will perform well either as wet or dry traps.

Since yellow jackets feed upon two basic types of materials, adults primarily on carbohydrates and larvae on proteins, a combination of the two is usually most effective as bait. However, excessive use of carbohydrates should be avoided as many of the beneficial hymenopterous insects, such as the honey bee, are also attracted to carbohydrates.

Glue boards have been used to trap yellow jackets. Here a substrate is provided with a combination of an attractant and a sticky material with permanent tack. When a yellow jacket lands on the glue board it becomes mired in the sticky material and can't fly away. Glue boards are a variation of the once popular fly paper.

One of the oldest ways of controlling yellow jacket populations involves suspending raw fish over a pan filled with water and a wetting agent. The skin of the fish is cut or broken to give the yellow jackets ready accesses to the flesh of the fish. Typically, a yellow jacket worker will cut a piece from the flesh of the fish and fly a short distance to trim the piece into a more manageable size. Frequently, however, the piece is too large for the yellow jacket to carry. If the yellow jacket refuses to release a large piece of fish, it falls into the pan of water and drowns. While these traps work well, they suffer from the disability of requiring frequent attention to rebate the traps with fresh fish and to replace the fish taken from the traps by carnivorous wildlife.

The instant invention does not depend upon a trap of any articular design. However, to illustrate the kind of traps in which the attractants for yellow jackets may used, reference is made, for example, to U.S. Pat. No. 3,803,753. Here there is disclosed a container, such as an ordinary can or jar, with a removable lid. As illustrated in the drawings of the patent, the lid has a number of holes about 0.5 inches in diameter at spaced intervals around the periphery. Yellow jackets can crawl through the holes but can't find their way out.

The bait suggested for use in the '753 patent is a fish-flavored proteinaceous food, such as cat food, flavoring and a small amount of a toxicant dissolved in the food.

U.S. Pat. No. 4,551,941 is an example of a configuration for a trap that is also useful in the practice of this invention. Here a transparent cylindrical insect trap is disclosed that provides a bottom entry to a circular truncated entry cone. The small end of the cone terminates within the cylindrical entrapment chamber. A screened orifice is provided to permit the escape of volatile olfactory attractants. The patent advises that colors may be used with advantage as optical attractants.

DISCLOSURE OF THE INVENTION

It is the principal object of the invention to provide attractants for yellow jackets that are more effective than those known in the prior art.

A related object of the invention is to provide an attractant for yellow jackets that is effective to attract more varieties of the common species of yellow jackets.

It is also an object of the invention to provide an attractant for yellow jackets that can be used effectively in diverse geographic regions.

Another object of the invention is to provide an attractant that can be used to good effect in either "dry" or "wet" traps.

Another object of the invention is to provide an attractant for yellow jackets that is safe, non-toxic and environmentally friendly.

Another object of the invention is to provide an attractant for use in traps for yellow jackets that has a long shelf life, is stable in use over prolonged periods of time and requires minimum attention or maintenance.

Yet another object of the invention is to provide an attractant that is effective over several phases in the life cycles of yellow jacket colonies, such as, for example, when either protein or carbohydrate foods are most in demand.

Still another object of the invention is to provide an effective attractant for yellow jackets that will not be harmful to hymenopterous insects.

These and other objects of the invention are achieved by the addition of a weak acid to known formulations for yellow jacket attractants. While the addition of a weak acid has proven beneficial in improving the effectiveness of many different formulations for yellow jacket attractants, mixtures of saccharides and proteins are the preferred attractants for use in the invention. In these preferred attractants apple juice concentrate may be utilized as the saccharide and powdered eggs or powdered poultry as the protein. A small amount of detergent added to water provides a convenient drowning solution.

The addition of a small amount of a weak acid to yellow jacket attractants has shown significant improvements in attracting a considerable range of yellow jacket species, in proving effective during the several phases of a yellow jackets life cycle and in not attracting beneficial hymenopterous insects. It is believed that no yellow jacket attractants are known that combine these desirable properties so effectively.

Dilute acetic acid is a useful weak acid for use in the practice of the invention and vinegar is a convenient and readily available source. It is noted that U.S. Food and Drug Administration proscribe that, unless otherwise modified, the term "vinegar" refers to a product derived from apples which contains at least 5 g. of acetic acid per 100 ml. of product. Other sources define a "vinegar" as a compound that contains about 5 g acetic acid without regard to its source. For example, the *Concise and Technical Dictionary* of the Chemical Publishing Company, Inc. dated 1947 defines "vinegar" as a "Solution containing a minimum if 4% acetic acid, produced by the bacterial oxidation of alcoholic liquors.

Best Means of Practicing the Invention

In the Examples and reported test results that follow, traps were usually hung in trees approximately four to six feet above the ground. A number of traps were used in each area where tests were made and the traps were spaced anywhere from fifteen to fifty feet apart. The traps used were commercially available traps generally of the top opening lid variety. Holes were made in the lids which were large enough to allow a yellow jacket to crawl inside the trap but small enough to confuse the yellow jackets in finding their way out. A trap of this kind is commercially available from Woodstream, Inc. sold under its trade name Yellow Jacket Trap®. The "vinegar" used in the examples was a vinegar as defined by FDA being a 5% acetic acid solution derived from apples. The "preferred formulation" used in the below reported trials was comprised of 58% apple juice concentrate; 36% vinegar; 5% poultry liver; and 1% dish detergent.

Observed Test Trials

Trials "A"

In an attempt to quantify the amount of vinegar that provides optimum results, vinegar was added to the preferred formulation of the invention and the average number of yellow jackets caught in the traps in three trials yielded the following results (here as elsewhere in the specification and claims, all percentages are given as weight percentages):

| | |
|---|---|
| 0% vinegar | 17 yellow jackets |
| 10% vinegar | 37 yellow jackets |
| 36% vinegar | 45 yellow jackets |
| 90% vinegar | 12 yellow jackets |

Trials "B"

Test were conducted on the west coast to compare the effectiveness of the preferred formulation of the invention with commercial formulations containing heptyl butyrate. Two trials of each formulation were made and the numbers indicate the average number of yellow jackets caught in the trials.

| | |
|---|---|
| Apple Juice Concentrate + Powdered Poultry Liver + Vinegar + Detergent | 161 |
| Heptyl Butyrate | 64 |
| Heptyl Butyrate + Apple Juice Concentrate + Protein | 85 |

These tests are of particular significance since heptyl butyrate has historically always been considered the best attractant for yellow jackets indigenous to the west coast (*V. pensylvanica*). These trials indicate that formulations of this invention perform better than do those that include heptyl butyrate.

Trials "C"

The results shown in the below TABLE "1" show the number of the yellow jackets caught in a locations in Florida and Pennsylvania in similar, spaced apart traps. The results in Florida are based on an average of three trials and the results in Pennsylvania are based upon the average of four trials.

TABLE 1

| ATTRACTANT | FLORIDA (SQUAMOSA) | PENNSYLVANIA (GERMANICA) |
|---|---|---|
| Preferred Formulation of the Invention (58% apple juice concentrate, 36% vinegar; 5% poultry liver; 1% dish detergent.) | 105 | 74 |

TABLE 1-continued

| ATTRACTANT | FLORIDA (SQUAMOSA) | PENNSYLVANIA (GERMANICA) |
|---|---|---|
| Best Performing Prior Art Formulations | 53 | 39 |
| Apple Juice | 22 | 13 |
| Apple Juice Concentrate | 14 | 5 |
| Grenadine | 12 | 8 |
| Apple Cider Vinegar | 10 | 9 |
| Heptyl Butyrate + Protein | 9 | 2 |
| Maple Syrup | 5 | N/A |
| Beer | 4 | 4 |
| Grape Drink | 3 | 1 |
| Coca Cola ® | 3 | N/A |
| Sugar Water | 1 | 0 |
| Lemonade | NIL | N/A |
| Turkey/Ham | NIL | N/A |
| Powdered poultry liver + water | NIL | 0 |

Trials "D"

Reference was earlier made to the fact that the attractants of this invention could be used to beneficial effect in traps either of the "dry" or "wet" trap types. In these trials, preferred formulations of this invention were conducted on the west coast.

Three trials were made with each of the traps. The "dry" traps containing the preferred attractant of the invention accumulated an average of 36 yellow jackets. Under similar times and conditions, wet traps containing the same attractant, diluted with 15 parts water by weight as a drowning solution, accumulated and average 38 yellow jackets. The small difference is well within experimental error.

From the foregoing, it can be understood that the following advantageous accrue in the practice of this invention:

- the attractants are effective over a number of species of yellow jackets;
- the attractants are effective during various yellow jacket feeding cycles;
- the attractants are effective whether used wet or dry;
- the attractants are effective over a prolonged period of time and have good shelf life;
- the attractants are benign to hymenopterous insects;
- the attractants are safe, non-toxic and environmentally friendly; and
- the attractants are effective when used in different geographic areas.

What is claimed is:

1. A method for attracting yellow jackets comprising:
   providing a composition that contains a yellow jacket attracting amount of a saccharide, a
   proteinaceous material, water and detergent;
   adding to said composition an amount of weak acid that improves the attractiveness of said composition to yellow jackets; and
   placing the composition in a container at a locus where yellow jackets need to be controlled.

2. The method according to claim 1, wherein the saccharide is apple juice or an apple juice concentrate.

3. The method according to claim 1, wherein the proteinaceous material is poultry liver or powdered egg.

4. The method according to claim 1, wherein the weak acid is dilute acetic acid.

5. The method according to claim 4, wherein the weak acid is vinegar.

6. The method according to claim 5, wherein the vinegar contains about 5% by weight acetic acid and is derived from apples.

7. An attractant composition for yellow jackets comprising a yellow jacket attracting amount of a saccharide, a proteinaceous material, water and detergent, wherein the composition further comprises a weak acid in an amount that improves the attractiveness of the composition to yellow jackets.

8. The composition according to claim 7, wherein the saccharide is apple juice or an apple juice concentrate.

9. The composition according to claim 7, wherein the proteinaceous material is poultry liver or powdered egg.

10. The composition according to claim 7, wherein the weak acid is dilute acetic acid.

11. The composition according to claim 10, wherein the weak acid is vinegar.

12. The composition according to claim 11, wherein the vinegar contains about 5% by weight acetic acid and is derived from apples.

13. The composition according to claim 7, wherein the water and detergent are present in sufficient amount to make a drowning solution.

14. An attractant composition for yellow jackets comprising a mixture of about 35% by weight vinegar, about 60% by weight apple juice concentrate, about 5% by weight poultry liver, water and detergent.

15. The composition according to claim 14, wherein the water and detergent are present or further added in sufficient amount to make a drowning solution.

* * * * *